(12) United States Patent
Nielsen

(10) Patent No.: US 6,448,056 B1
(45) Date of Patent: Sep. 10, 2002

(54) MICROBIAL XYLOGLUCAN ENDOTRANSGLYCOSYLASE (XET)

(75) Inventor: Ruby Illum Nielsen, Farum (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/045,494

(22) Filed: Mar. 20, 1998

Related U.S. Application Data (63) Continuation of application No. PCT/DK98/00076, filed on Feb. 26, 1998.
(60) Provisional application No. 60/051,016, filed on May 27, 1997.

(30) Foreign Application Priority Data

Feb. 26, 1997 (DK) ................................................ 0212/97

(51) Int. Cl.[7] ........................... C12P 21/06; C12N 9/00; C12N 9/10; C12N 1/20; C12N 1/14
(52) U.S. Cl. ....................... 435/193; 435/183; 435/200; 435/69.1; 435/252.3; 435/254.1
(58) Field of Search ................................ 435/183, 200, 435/202, 203, 206, 207, 208, 209, 210, 69.1, 193, 252.3, 254.1

(56) References Cited

FOREIGN PATENT DOCUMENTS

| | | |
|---|---|---|
| EP | 0 562 836 | 9/1993 |
| WO | WO 95/13384 | 5/1995 |

OTHER PUBLICATIONS

Fanutti et al. The Plant Journal, 1993, vol. 3(5):691–700.*
Honda et al., Appl Microbiol Biotechnol, vol. 25, pp. 480–483 (1987).
Honda et al., Appl Microbiol Biotechnol, vol. 29, pp. 264–268 (1988).
Maidak et al., Nucleic Acids Research, vol. 22, No. 17, pp. 3485–3487 (1994).
Dialog, Fry et al., Chemical Abstract (1997).
Fry et al. Biochem. J. (1992) vol. 282(3):821–828.

* cited by examiner

Primary Examiner—Rebecca E. Prouty
Assistant Examiner—Manjunath N. Rao
(74) Attorney, Agent, or Firm—Elias Lambiris; Jason Garbell (57) ABSTRACT

It has been found by a screening assay that XET activity is produced by an overwhelming array of phylogenetically dispersed microorganisms. Accordingly, the present invention relates to a xyloglucan endotransglycosylase preparation which is producible by cultivation of a microorganism expressing an XET.

23 Claims, 2 Drawing Sheets

MICROBIAL XYLOGLUCAN ENDOTRANSGLYCOSYLASE (XET)

CROSS-REFERENCE TO RELATED APPLICATIONS

This application is a continuation of PCT/DK98/00076 filed Feb. 26, 1998 and claims priority under 35 U.S.C. 119 of Danish application serial no. 0212/97 filed Feb. 2, 1997, and U.S. provisional application No. 60/051,016 filed May 27, 1997 the contents of which are fully incorporated herein by reference.

FIELD OF THE INVENTION

The present invention relates to microbial xyloglucan endotransglycosylases (XETs) and the production and uses thereof.

BACKGROUND OF THE INVENTION

Xyloglucan endotransglycosylase (XET) is an enzyme known from plants. To our best knowledge XET has never been described from microorganisms.

Stephen C. Fry et al. suggest in *Biochem. J* (1992) 282, p. 821–828 that XET is responsible for cutting and rejoining intermicrofibrillar xyloglucan chains and that XET thus causes the wall-loosening required for plant cell expansion.

XET has been suggested for use in regulating the morphology of a plant, see EP 562 836 p. 2 1. 27–28.

XET is believed to be present in all plants, in particular in all land plants. XET has been extracted from dicotyledons, monocotyledons, in particular graminaceous monocotyledons and liliaceous monocotyledons, and also from a moss and a liverwort, for reference see *Biochem. J* (1992) 282, p. 823.

In the copending patent application PCT/DK 96/00538 (WO 97/23683) we have shown that a cellulosic material may get improved strength properties and/or improved shape-retention properties and/or improved anti-wrinkling properties after treatment with an XET enzyme.

The XET enzyme has some very interesting applications, so it is an object of the present invention to provide microbially derived xyloglucan endotransglycosylases useful for, e.g., the applications described above. The microbially derived xyloglucan endotransglycosylases would have the great advantage that they could easily be produced in great quantities.

BRIEF DISCLOSURE OF THE INVENTION

It has been found by a screening assay that XET activity is produced by an overwhelming array of phylogenetically dispersed microorganisms.

Accordingly, the present invention relates to a xyloglucan endotransglycosylase preparation which is producible by cultivation of a microorganism expressing an XET; in particular the present invention relates to:

A method for the production of a xyloglucan endotransglycosylase enzyme (XET) comprising
(a) culturing in a suitable nutrient medium a microorganism expressing a microbial XET under conditions conducive to the production of the XET enzyme, and
(b) subsequently recovering of the XET enzyme from the nutrient medium.

Further, the present invention relates to use of the XET preparation of the present invention for treating cellulosic material, and to microbial XET preparations as such.

BRIEF DESCRIPTION OF DRAWINGS

The present invention is further illustrated by reference to the accompanying drawing, in which.

DETAILED DISCLOSURE OF THE INVENTION

The present invention relates to a xyloglucan endotransglycosylase preparation which is producible by cultivation of a microorganism.

It has been shown in the present application that XET is produced by fungi and bacteria, and it is contemplated that XET is also produced by yeasts.

An "XET-paper" was used for identifying XET producing microorganisms. The "XET-paper" is described in the copending patent application PCT/GB96/02351 (WO 97/11193); it is a xyloglucan-coated paper which is dipped through a labelled oligosaccharide.

The labelled oligosaccharide, the xyloglucan-impregnated paper, and the dot-blot test for XET activity were made in the following way:
Preparation of Labelled Oligosaccharide The reducing oligosaccharide 4-O-[4-O-[4-O-[6-O-α-D-Xylopyranosyl-β-D-glucopyranosyl]-6-O-(2-O-β-D-galactopyranosyl)-α-D-xylopyranosyl-β-D-glucopyranosyl]-6-O-(2-O-β-D-galactopyranosyl)-α-D-xylopyranosyl-β-D-glucopyranosyl]-D-glucose ("XLLG") (1 gram) is dissolved in 25 ml of a saturated aqueous solution of ammonium hydrogencarbonate containing 1 gram of sodium cyanoborohydride ($NaCNBH_3$) and incubated in the dark at 25° C. for 7 days to permit reductive amination. The ammonium hydrogencarbonate is then removed by drying, and the (ninhydrin-reactive) aminated derivative of XLLG is purified e.g. by gel-permeation chromatography or cation-exchange chromatography. The product is believed to be an oligosaccharidyl-1-amino-1-deoxyalditol, i.e. a derivative of XLLG in which the reducing terminal D-glucose moiety has been replaced by 1-amino-1-deoxy-D-glucitol.

The oligosaccharidyl-1-amino-1-deoxyalditol (50 mg) is dissolved in 3 ml of 3% borax (di-sodium tetraborate; pH=9.0–9.5) and a freshly-prepared solution of 10 mg lissamine rhodamine sulphonyl chloride [purchased from Molecular Probes Inc., USA] in 0.75 ml of dry dimethylformamide (DMF) is added gradually, with stirring, and the mixture is incubated in the dark overnight. A further 0.75 ml of DMF containing 10 mg lissamine rhodamine sulpohnyl chloride is added and the mixture incubated for a further 8 h. The bright pink oligosaccharidyl-1-amino-1-deoxyalditol-lissamine-rhodamine conjugate (XLLGol-SR) is purified by gel-permeation chromatography followed by reversed-phase chromatography on a $C_{18}$-silica gel column. After washing of the latter column with water, a methanol gradient is applied and the XLLGol-SR elutes in about 50% methanol.

Preparation of Xyloglucan-impregnated Paper

Whatman No.1 filter paper is moistened with a 1% aqueous solution of xyloglucan and dried. The XLLGol-SR preparation is diluted into enough 75% aqueous acetone to give an absorbance at 580 nm ($A_{580}$) of 0.2; the xyloglucan-coated sheet of Whatman No. 1 paper is then dipped through this solution and re-dried; the product is referred to as "XET-paper". Suitably sized pieces (e.g. 72×108 mm) of the XET-paper may then be glued with a non-aqueous adhesive onto a non-absorbent medium such as a sheet of transparent acetate.

Dot-Blot Test for XET Activity (i) A spot of the solution to be tested for XET-activity is pipetted on to a marked position in a piece of XET-paper. If the spots are 4 μl, the spacing between the samples can conveniently be 9 mm (centre-to-centre, i.e. as in a standard 96-well test plate format).

(ii) The XET paper is then quickly (before the spots have dried) clamped between two sheets of plastic (e.g. acetate sheets, as used on overhead projectors) and incubated e.g. at 20° C. for 1 hour.

(iii) The incubated XET-paper and its plastic backing is then placed (paper-side down) in a dish containing about 150 ml of a solvent [e.g. freshly prepared ethanol/formic acid/water (1:1:1 by volume)] that will remove from the paper the unreacted XLLGol-SR but not any XLLGol-SR that has become incorporated into the xyloglucan owing to XET-catalysed transglycosylation. The paper now readily detaches from the plastic backing.

(iv) The paper is then rinsed in running water for 5 minutes, then in approximately 100 ml of acetone for 5 minutes, and then dried thoroughly. If desired, drying can be expedited by a 5-minute treatment in an oven at 80° C.

(v) The paper is then examined under a short-wavelength ultraviolet lamp (e.g. emitting at 254 nm; suitable eye- and skin-protection should be worn). Active XET is indicated by a pink (orange-fluorescing) spot, which can be quantified, e.g. by use of a scanning spectrofluorimeter.

XET Enzymes

We have discovered that microbial enzymes with XET activity may be either transglycosylases (meaning that they lack hydrolase activity or only have a very low hydrolase activity) or they may catalyze both transglycosylation and hydrolysis of xyloglucan.

XET enzymes with both transglycosylating and hydrolytic activities are also described for XET enzymes obtained from plants (see Annu. Rev. Plant Physiol. Plant Mol. Biol.1995.46: p. 509).

Taxonomic Classification

The taxonomic classification used herein builds primarily on the system used in the :NIH Data Base (Entrez, version spring 1996) available on World Wide Web: (http://www3.ncbi.nlm.nih.gov/htbin/ef/entrezTAX).

Regarding classification of organisms which are not included in the Entrez data base the following generally available and world wide accepted reference books have been used:

For Ascomycetes: Eriksson, O. E. & Hawksworth, D. L.: Systema Ascomycetum vol 12 (1993).

For Basidiomycetes, Jülich, W.: Higher Taxa of Basidiomycetes, Bibliotheca Mycologia 85, 485pp (1981).

For Zygomycetes: O'Donnell, K.: Zygomycetes in culture, University of Georgia, US, 257pp (1979).

General Mycological Reference Books:

Hawksworth, D. L., Kirk, P. M., Sutton, B. C. and Pegler, D. N.: Dictionary of the fungi, International Mycological Institute, 616 pp (1995);

Von Arx, J. A.: The genera of fungi sporulating in culture, 424 pp (1981).

Preferred Fungi

In a preferred embodiment of the present invention the XET preparation is produced by cultivation of a fungus, in particular a fungus which belongs to Basidiomycota, Zygomycota, Ascomycota or a Mitosporic fungus.

A preferred Basidiomycota strain is a Hymenomycetes strain belonging to the orders Coriolales, Schizophyllales, Stereales or Xenasmatales; in particular a strain belonging to one of the families Coriolaceae, Corticiaceae, Schizophyllaceae, Stereaceae or Tubulicrinaceae. Preferred genera is one of the following: Trametes, Corticium, Schizophyllum, or Tubulicrinis. Preferred species is one of the following *Trametes hirsuta, Corticium roseum,* Schizophyllum sp, *Stereum hirsutum* or *Tubulicrinis subulatus.*

Preferred Ascomycota are strains belonging to the classes Loculoascomycetes, Discomycetes, Pyrenomycetes, and Plectomycetes, preferably those belonging to the orders Dothideales, Rhytismatales, Pezizales, Leotiales, Xylariales, Hypocreales, Halosphaeriales, Phyllachorales, Diaporthales and Eurotiales.

Preferred strains are strains belonging to the families Botryosphaeriaceae, Dothioraceae, Mycosphaerellaceae, Tubeufiaceae, Pleosporaceae, Leptosphaeriaceae, Rhytismataceae, Sarcosomataceae, Pyronemataceae, Ascobolaceae, Sclerotiniaceae, Amphisphaeriaceae, Xylariaceae, Hypocreaceae, Halosphaeriaceae, Phyllachoraceae, Valsaceae, Melanconidaceae and Trichocomataceae; especially strains belonging to the genera Diplodia, Plowrightia, Phyllosticta, Septoria, Tubeufia, Alternaria, Coniothyrium, Phoma, Embellisia, Tiarosporella, Galiella, Pseudoplectania, Pyronema, Oedocephalum, Botrytis, Aposphaeria, Pestalotia, Pestalotiopsis, Poronia, Nodulisporium, Xylaria, Fusarium, Verticilliurn, Volutella, Chaetapiospora, Lulworthia, Colletotrichum, Cytospora, Discula, Phomopsis, Coryneum, Seimatosporium, Aspergillus, Eurotium, Eupenicillium, Penicillium, Petromyces and Talaromyces.

Preferred are the species *Diplodia gossypina, Plowrightia ribesia,* Phyllosticta sp, Septoria sp, *Tubeufia amazonensis,* Alternaria sp, *Embellisia hyacinthi, Phoma neoloba, Phoma tropica,* Coniothyrium Sp, *Coniothyrium olivaceoum, Coniothyrium dunckii, Tiarosporella phaseolina,* Tiarosporella sp, *Galiella celebica, Pseudoplectania nigrella, Pyronema domesticum,* Oedocephalum sp, *Botrytis cinerea,* Aposphaeria sp, Pestalotia sp, Pestalotiopsis sp. *Poronia punctata,* Xylaria sp, Nodulisporium sp, *Fusarium solani,* Verticillium sp, *Volutella buxi, Chaetapiospora rhododendri, Lulworthia uniseptata, Colletotrichum aculatum, Colletotrichum crassipes,* Cytospora spp, Discula sp, *Phomopsis ilicis, Phomopsis cirsii, Coryneum castaneicola, Seimatosporium lichenicola, Aspergillus tamarii, Eurotium chevalieri, Eupenicillium javanicum, Penicillium capsulatum, Penicillium olsonii, Penicillium pinophilum, Penicillium roqueforti, Penicillium italicum, Penicillium canescens, Penicillium verruculosum, Petromyces alliaceus* and *Talaromyces flavus.*

Examples of useful Zygomycota are strains belonging to the order Mucorales, preferably strains belonging to the families Chaetocladiaceae and Mucoraceae.

Preferred strains belong to the genera Dichotomocladium, Actinomucor, Gongronella, Sporodiniella and Mucor, in particular *Dichotomocladium hesseltinei, Actinomucor elegans, Gongronellla butleri, Sporodiniella umbellata* and *Mucor miehei* var minor.

Example of a strain of uncertain taxonomy is *Vialaea insculpta.*

Examples of strains belonging to the Mitosporic Fungi are *Acrodontium crateriforme, Aureobasidium pullulans,* Circinotrichum sp, Cryptocline sp. Ellisiopsis sp, *Epicoccum nugrum,* Gliocladium sp, *Helicorhoidion irregulare,* Hendersonia spp, Mariannaea sp, Microsphaeropsis sp, Ramularia sp, Sarcopodium sp, Spadicoides sto, *Speiropsis pedatospora, Sporotrichum exile,* Stilbella sp, Trichothecium sp, *Trimmatostroma abietes, Tubakia dryina,* Wiesneriomyces sp and *Zygosporium masonii.*

Preferred Bacteria

In another aspect, the invention relates to a novel XET preparation which is producible by cultivation of a bacterium.

Preferred bacteria are gram-negative or gram-positive.

Examples of XET-producing gram-positive bacteria are strains belonging to the genus Bacillus.

Preferred Strains

The following strains have been found to be XET-positive:

1. *Dichotomocladium hesseltinei.* Acc No of strain: CBS 164.61. Classification: Zygomycota, Mucorales, Chaetocladiaceae.
2. *Actinomucor elegans.* Ex of Acc No of strain: CBS 154.86. Classification: Zygomycota, Mucorales, Chaetocladiaceae.
3. *Mucor miehei* var minor. Acc No of strain: ATCC 36018. Classification: Zygomycota, Mucorales, Mucoraceae.
4. *Gongronella butleri.* A strain of *Gongronella butleri* has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 448.97. Classification: Zygomycota, Mucorales, Chaetocladiaceae.
5. *Sporodiniella umbellata.* Acc No of strain: CBS 195.77. Classification: Zygomycota, Mucorales, Mucoraceae.
6. Phyllosticta sp. Isolated from a leaf of Pithecolobium sp from China. Classification: Ascomycota, Loculoascomycetes, Dothidiales, Mycosphaellaceae.
7. Septoria sp. A strain of Septoria sp has been deposited according to the Budapest Treaty on the International Recognition of the Deposits of Microorganisms for the Purpose of Patent Procedures, on Jan. 2, 1996, at Centraalbureau voor Schimmelcultures (CBS), under Accession No. CBS 831.95. Classification: Ascomycota, Loculoascomycetes, Dothidiales, Mycosphaellaceae.
8. *Diplodia gossypina.* A strain of *Diplodia gossypina* has been deposited according to the Budapest Treaty on the International Recognition of the Deposits of Microorganisms for the Purpose of Patent Procedures, on Mar. 12, 1996, at Centraalbureau voor Schimmelcultures (CBS), under Accession No. CBS 274.96. Classification: Ascomycota, Loculoascomycetes, Dothidiales, Botrysphaeriaceae.
9. *Plowrightia ribesia.* Isolated from Ribes sp., Denmark. Classification: Ascomycota, Loculoascomycetes, Dothidiales, Dothioraceae.
10. *Tubeufia amazonensis.* Acc No of Strain: ATCC 42524. Classification: Ascomycota, Loculoascomycetes, Dothidiales, Tubeufiaceae.
11. Alternaria sp. Classification: Ascomycota, Loculoascomycetes, Dothidiales, Pleosporaceae.
12. *Embellisia hyacinthi.* Acc No of species IMI 211561. Classification: Ascomycota, Loculoascomycetes, Dothidiales, Pleosporaceae.
13. *Phoma neoloba.* Classification: Ascomycota, Loculoascomycetes, Dothideales, Pleosporaceae.
14. *Phoma tropica.* Ex on Acc No of species CBS 537.66. Classification: Ascomycota, Loculoascomycetes, Dothideales, Pleosporaceae.
15. Coniothyrium sp. Classification: Ascomycota, Loculoascomycetes, Dothideales, Leptosphaeriaceae.
16. *Coniothyrium olivaceoum.* Ex on Acc No of species CBS 304.68. Classification: Ascomycota, Loculoascomycetes, Dothideales, Leptosphaeriaceae.
17. *Coniothyrium dunckii.* Classification: Ascomycota, Loculoascomycetes, Dothideales, Leptosphaeriaceae.
18. *Tiarosporella phaseolina.* A strain of *Tiarosporella phaseolina* (Macrophomina sp) has been deposited according to the Budapest Treaty on the International Recognition of the Deposits of Microorganisms for the Purpose of Patent Procedures, on the Jan. $28^{th}$, 1997, at Centraalbureau voor Schimmelcultures (CBS) under Accession No. CBS 446.97. Classification: Ascomycota, Discomycetes, Rhytismatales, Rhytismataceae.
19. Tiarosporella sp. Classification: Ascomycota, Discomycetes, Rhytismatales, Rhytismataceae.
20. *Galiella celebica.* Isolated from a sample collected in Japan. Classification: Ascomycota, Discomycetes, Pezizales, Sarcosomataceae.
21. *Pseudoplectania nigrella.* A strain of *Pseudoplectania nigrella* has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 444.97. Classification: Ascomycota, Discomycetes, Pezizales, Sarcosomataceae.
22. *Pyronema domesticum.* Isolated from a sample from Norway. Classification: Ascomycota, Discomycetes, Pezizales, Pyronemataceae.
23. Oedocephalum sp. Classification: Ascomycota, Discomycetes, Pezizales, Ascobolaceae.
24. *Botrytis cinerea.* A strain of *Botrytis cinerea* has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 447.97. Classification: Ascomycota, Discomycetes, Leotiales, Sclerotiniaceae.
25. Aposphaeria sp. Classification: Ascomycota, Discomycetes, Leotiales, Sclerotiniaceae.
26. Pestalotia sp. A strain of Pestalotia sp. has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 445.97. Classification: Ascomycota, Pyrenomycetes, Xylariales, Amphisphaeriaceae.
27. Pestalotiopsis sp. Classification: Ascomycota, Pyrenomycetes, Xylariales, Amphisphaeriaceae.
28. *Poronia punctata.* Isolated from a sample from Sweden. Classification: Ascomycota, Pyrenomycetes, Xylariales, Xylariaceae.
29. Xylaria sp. Isolated from a leaf of the palm, *Sabal jamaicensis,* growing in Mona, Jamaica. Classification: Ascomycota, Pyrenomycetes, Xylariales, Xylariaceae Xylariaceae.
30. Nodulisporium sp. Classification: Ascomycota, Pyrenomycetes, Xylariales, Xylariaceae.
31. *Fusarium solani.* Isolated from a sample of grain of maize from India. Classification: Ascomycota, Pyrenomycetes, Hypocreales, Hypocreaceae.
32. Verticillium sp. A strain of Verticillium sp has been deposited according to the Budapest Treaty on the International Recognition of the Deposits of Microorganisms for the Purpose of Patent Procedures, on Jan. 2, 1996, at Centraalbureau voor Schimmelcultures (CBS), under Accession No. CBS 830.95. Classification: Ascomycota, Pyrenomycetes, Hypocreales, Hypocreaceae.

33. *Volutella buxi.* Acc No of Strain: IMI 049467. Classification: Ascomycota, Pyrenomycetes, Hypocreales, Hypocreaceae.

34. *Chaetapiospora rhododendri.* Classification: Ascomycota, Pyrenomycetes, Xylariales, Xylariaceae, Hyponectriaceae.

35. *Lulworthia uniseptata.* A strain of *Lulworthia uniseptata* has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 442.97. Classification: Ascomycota, Pyrenomycetes, Halosphaeriales, Halosphaeriaceae.

36. *Colletotrichum aculatum.* Classification: Ascomycota, Pyrenomycetes, Phyllachorales, Phyllachoraceae.

37. *Colletotrichum crassipes.* Classification: Ascomycota, Pyrenomycetes, Phyllachorales, Phyllachoraceae.

38. Cytospora sp. A strain of Cytospora sp has been deposited according to the Budapest Treaty on the International Recognition of the Deposits of Microorganisms for the Purpose of Patent Procedures, on Jan. 23, 1997, at Centraalbureau voor Schimmelcultures (CBS), under Accession No. CBS 424.97. Classification: Ascomycota, Pyrenomycetes, Diaporthales, Valsaceae.

39. Cytospora sp. A strain of Cytospora sp has been deposited according to the Budapest Treaty on the International Recognition of the Deposits of Microorganisms for the Purpose of Patent Procedures, on Jan. 23, 1997, at Centraalbureau voor Schimmelcultures (CBS), under Accession No. CBS 425.97. Classification: Ascomycota, Pyrenomycetes, Diaporthales, Valsaceae.

40. Discula sp. Classification: Ascomycota, Pyrenomycetes, Diaporthales, Valsaceae.

41. *Phomopsis ilicis.* Classification: Ascomycota, Pyrenomycetes, Diaporthales, Valsaceae.

42. *Phomopsis cirsii.* Classification: Ascomycota, Pyrenomycetes, Diaporthales, Valsaceae.

43. *Coryneum castaneicola.* Classification: Ascomycota, Pyrenomycetes, Diaporthales, Melanconidaceae.

44. *Seimatosporium lichenicola.* Classification: Ascomycota, Pyrenomycetes, Diaporthales, Melanconidaceae.

45. *Aspergillus tamarii.* Ex of Acc No of strain: CBS 821.72. Classification: Ascomycota, Plectomycetes, Trichocomataceae.

46. *Eurotium chevalieri.* Ex of Acc No of strain: CBS 472.91. Classification: Ascomycota, Plectomycetes, Eurotiales, Trichocomataceae.

47. *Penicillium capsulatum.* Ex of Acc No of strain: CBS 273.86. Classification: Ascomycota, Plectomycetes, Eurotiales, Trichocomataceae.

48. *Penicillium olsonii.* Ex of Acc No of strain: CBS 523.89. Classification: Ascomycota, Plectomycetes, Eurotiales, Trichocomataceae.

49. *Penicillium pinophilum.* Ex of Acc No of strain: CBS 440.89. Classification: Ascomycota, Plectomycetes, Eurotiales, Trichocomataceae.

50. *Penicillium roqueforti.* Ex of Acc No of strain: CBS 167.91. Classification: Ascomycota, Plectomycetes, Eurotiales, Trichocomataceae.

51. *Penicillium italicum.* Ex of Acc No of strain: IMI 078 681. Classification: Ascomycota, Plectomycetes, Eurotiales, Trichocomataceae.

52. *Penicillium canescens.* Ex of Acc No of strain: CBS 579.70. Isolated from a salt mine in Egypt. Classification: Ascomycota, Plectomycetes, Eurotiales, Trichocomataceae.

53. *Eupenicillium javanicum.* Ex of Acc No of the strain: CBS 448.74. Classification: Ascomycota, Plectomycetes, Eurotiales, Trichocomataceae.

54. *Penicillium verruculosum.* Ex of Acc No of strain: CBS 563.92. Classification: Ascomycota, Plectomycetes, Eurotiales, Trichocomataceae.

55. *Talaromyces flavus.* Acc No of the strain: ATCC 52201. Classification: Ascomycota, Plectomycetes, Eurotiales, Trichocomataceae.

56. *Petromyces alliaceus.* Acc No of strain: CBS 511.69. Classification: Ascomycota, Plectomycetes, Eurotiales, Trichocomataceae.

57. *Trametes hirsuta.* Isolated from a sample collected in Denmark. Classification: Basidiomycota, Hymenomycetes, Coriolales, Coriolaceae.

58. Schizophyllum sp. A strain of Schizophyllum sp has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 443.97. Classification: Basidiomycota, Hymenomycetes, Schizophyllales, Schizophyllaceae.

59. *Corticium roseum.* Isolated from a sample collected in Denmark. Classification: Basidiomycota, Hymenomycetes, Aleurodiscales Cortiaceae.

60. *Tubulicrinis subulatus.* Isolated from a sample collected in Denmark. Classification: Basidiomycota, Hymenomycetes, Xenasmatales, Tubulicrinaceae.

61. *Stereum hirsutum.* Isolated from a sample collected in Denmark. Classification: Basidiomycota, Hymenomycetes, Stereales, Stereaceae.

62. *Acrodontium crateriforme.* Classification: Mitosporic fungus.

63. *Aureobasidium pullulans.* Classification: Mitosporic fungus.

64. Circinotrichum sp. Classification: Mitosporic fungus.

65. Cryptocline sp. Classification: Mitosporic fungus.

66. Ellisiopsis sp. Classification: Mitosporic fungus.

67. *Epicoccum nigrum.* Classification. Mitosporic fungus.

68. Gliocladium sp. Classification: Mitosporic fungus.

69. *Helicorhoidion irregulare.* Classification: Mitosporic fungus.

70. Hendersonia sp. Classification: Mitosporic fungus.

71. Mariannaea sp. Classification: Mitosporic fungus.

72. Microsphaeropsis sp. Classification: Mitosporic fungus.

73. Ramularia sp. Classification: Mitosporic fungus.

74. Sarcopodium sp. Classification: Mitosporic fungus.

75. Spadicoides sto. Acc No of strain IMI203428. Classification: Mitosporic fungus.

76. *Speiropsis pedatospora.* Classification: Mitosporic fungus.

77. *Sporotrichum exile.* Acc No of strain CBS 350.47. Classification: Mitosporic fungus.

78. Stilbella sp. Classification: Mitosporic fungus.

79. Trichothecium sp. Classification: Mitosporic fungus.

80. *Trimmatostroma abietes.* Classification: Mitosporic fungus.

81. *Tubakia dryina.* Classification: Mitosporic fungus.

82. Wiesneriomyces sp. Classification: Mitosporic fungus.

83. *Zygosporium masonii.* Classification: Mitosporic fungus.

84. *Vialaea insculpta.* Classification: Uncertain.

85. *Bacillus alcalophilus.* A strain of *Bacillus alcalophilus* has been deposited according to the Budapest Treaty on the International Recognition of the Deposits of Microorganisms for the Purpose of Patent Procedures, on Feb. 12, 1997, at Deutsche Sammlung von Mikroorganismen und Zellkulturen GmbH, under Accession No. DSM 11404.

Production of XET

The XET enzyme of the invention may be produced by aerobic cultivation of the above mentioned microbial strains on a nutrient medium containing suitable carbon and nitrogen sources, such media being known in the art.

Alternatively, the XET enzyme of the invention may be produced by aerobic cultivation of a transformed host organism containing the appropriate genetic information from, e.g., one of the above mentioned strains. Accordingly, the present invention also relates to a method for the production of a xyloglucan endotransglycosylase enzyme (XET) comprising (a) culturing in a suitable nutrient medium a transformed host microorganism expressing a microbial XET under conditions conducive to the production of the XET enzyme, and (b) subsequently recovering of the XET enzyme from the nutrient medium.

Such transformants can be prepared and cultivated by methods known in the art:

Cloning a DNA Sequence Encoding XET

The DNA sequence encoding a XET enzyme of the invention may be isolated from any microorganism producing the XET in question, using various methods well known in the art.

First, a genomic DNA and/or cDNA library should be constructed using chromosomal DNA or messenger RNA from the organism that produces the XET to be studied. Then, if the amino acid sequence of the XET is known, homologous, labelled oligonucleotide probes may be synthesized and used to identify XET-encoding clones from a genomic library or cDNA prepared from the organism in question. Alternatively, a labelled oligonucleotide probe containing sequences homologous to a known XET gene could be used as a probe to identify XET-encoding clones, using hybridization and washing conditions of lower stringency.

Yet another method for identifying XET-encoding clones would involve inserting fragments of genomic DNA or cDNA into an expression vector, such as a plasmid, transforming XET-negative host organism with the resulting DNA library, then plating the transformed cells onto agar plates and by use of the assay described above allowing clones expressing the XET to be identified.

Alternatively, the DNA sequence encoding the enzyme may be prepared synthetically by established standard methods, e.g. the phosphoamidite method described by S. L. Beaucage and M. H. Caruthers in *Tetrahedron Letters* 22, 1981, pp. 1859–1869 or the method described by Matthes et al. in *The EMBO J.* 3, 1984, pp. 801–805. In the phosphoamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. in *Science* 239, 1988, pp. 487–491.

Expression of XET

According to the invention, a XET-encoding DNA sequence produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding a XET enzyme of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a XET of the invention, especially in a bacterial host, are the promoter of the lac operon of *E.coli,* the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the Bacillus Amylolique-faciens α-amylase (amyQ), the promoters of the *Bacillus subtilis* xylA and xylB genes etc. For transcription in a fungal host, examples of useful promoters are those derived from the gene encoding A. oryzae TAKA amylase, *Rhizomucor miehei* aspartic proteinase, A. niger neutral α-amylase, A. niger acid stable α-amylase, A. niger glucoamylase, *Rhizomucor miehei* lipase, A. oryzae alkaline protease, A. oryzae triose phosphate isomerase or A. nidulans acetamidase.

The expression vector of the invention may also comprise a suitable transcription terminator and, in eukaryotes, polyadenylation sequences operably connected to the DNA sequence encoding the XET enzyme of the invention. Termination and poly-adenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *B. subtilis* or *B. licheniformis,* or one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular.

Procedures suitable for constructing vectors of the invention encoding a XET enzyme and containing the promoter, terminator and other elements, respectively, are well known to persons skilled in the art (cf., for instance, Sambrook et al. in *Molecular Cloning: A Laboratory Manual,* 2nd Ed., Cold Spring Harbor, 1989).

The cell of the invention, either comprising a DNA construct or an expression vector of the invention as defined above, is advantageously used as a host cell in the recombinant production of a XET of the invention. The cell may be transformed with the DNA construct of the invention encoding the XET conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are grampositive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gramnegative bacteria such as *E.coli.* The transformation of the bacteria may, for instance, be effected by protoplast transformation or by using competent cells in a manner known per se.

The yeast organism may favourably be selected from a species of Saccharomyces or Schizosaccharomyces, e.g., *Saccharomyces cerevisiae.* The filamentous fungus may advantageously belong to a species of Aspergillus, e.g., *Aspergillus oryzae* or *Aspergillus niger.* Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing a XET enzyme of the invention, which method comprises cultivating a host cell as described above under conditions conducive to the production of the XET and recovering the XET from the cells and/or culture medium.

The medium used to cultivate the cells may be any conventional medium suitable for growing the host cell in question and obtaining expression of the XET of the invention. Suitable media are available from commercial suppliers or may be prepared according to published recipes (e.g., as described in catalogues of the American Type Culture Collection).

The XET secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

According to the present invention a cellulosic material may get improved strength properties and/or improved shape-retention properties and/or improved anti-wrinkling properties after treatment with a XET enzyme. The XET enzyme has the ability to rearrange and link the xyloglucan molecules which are hydrogen bonded to the cellulosic fibres whereby the above mentioned features may be achieved.

In order to enhance the effect of the XET enzyme it may in some cases be an advantage to add xyloglucan to the cellulosic material whereby the enzyme may be able to link more cellulosic material together.

The treatment of the cellulosic material with the XET enzyme may be carried out in water, or it may be carried out in water in the presence of certain components such as a buffer and/or a wetting agent and/or a stabilizer and/or a polymer and/or an organic component reducing the water activity such as DMSO.

The buffer may suitably be a phosphate, borate, citrate, acetate, adipate, triethanolamine, monoethanolamine, di-ethanolamine, carbonate (especially alkali metal or alkaline earth metal, in particular sodium or potassium carbonate, or ammonium and HCl salts), diamine, especially diaminoethane, imidazole, Tris or amino acid buffer.

The wetting agent serves to improve the wettability of the cellulosic material. The wetting agent is preferably of a non-ionic surfactant type.

The stabilizer may be an agent stabilizing the XET enzyme.

According to the invention the concentration of XET in the aqueous medium may be 0.01–1000 $\mu$g of enzyme protein per g cellulosic material, preferably 0.05–100 $\mu$g of enzyme protein per g cellulosic material.

It will generally be appropriate to incubate the reaction medium (containing the cellulosic material and the XET enzyme) for a period of at least a few minutes. An incubation time of from 1 minute to 20 hours will generally be suitable, in particular an incubation time of from 30 minutes to 10 hours will often be preferred.

The temperature of the reaction medium in the process of the invention may suitably be in the range of 10–90° C., in particular in the range of 15–70° C., as appropriate for the XET enzyme in question.

The invention is further illustrated in the following non-limiting examples.

EXAMPLE 1

Screening for Positive XET Strains

Media

PD Agar: 39 g potato dextrose agar, DIFCO 0013; add deionized water up to 1000 ml, autoclave at 121° C. for 15–20 min.

YPG agar: 4 g yeast extract (DIFCO 0127), 1 g $KH_2PO_4$ (Merck 4873), 0.5g $MgSO_4.7H_2O$ (Merck 5886) 15 g dextrose (Roquette 101-0441) 20 g agar (Merck 1614) deionized water up to 1000 ml Autoclave at 121° C. for 15–20 min.

MEA: 20 g malt extract powder (Difco 0186) 1 g peptone (Difco 0118) 20 g glucose (Roquette France 1010441) 20 g agar (Merck 1614) deionized water up to 1000 ml Autoclave at 121° C. for 15 min Medium A. Per flask: 30 g wheat bran, 45 ml of the following solution: 10 g rofec (Roquette 101-0441), 10 g $NH_4NO_3$ (Merck 1187), 10 g $KH_2PO_4$ (Merck 4873), 40 g Solcafloc (Dicacel availabe from Dicalite-Europe-Nord, 9000 Gent, Belgium), 0.75 g $MgSO_4.7H_2O$ (Merck 5886), 15 g $CaCO_3$, tap water to 1000 ml, pH adjusted to 6.5.
Autoclave for 40 min at 121° C.
Medium B. 20 g soyabean meal, 5 g maltodex 01, (Roquette 101-7845), 15 g wheat bran, 3 g peptone (Difco 0118), 10 g cellulose avicel (Merck 2331), 0.2 ml pluronic (PE-6100, 101-3068), 1 g olive oil, deionized water up to 1000 ml.
100 ml in 500 ml Erlenmeyer flask with 2 baffles. Autoclave at 121° C. for 40 min.
Medium C. 100 g sucrose, 40 g soybean meal, 10 g $Na_2HPO_4. 12H_2O$ (Merck 6579), 0.1 ml pluronic (PE 6100), tap water up to 1000 ml. 0.5 g $CaCO_3$ in a 2 baffled Erlenmeyer flask with 100 ml medium. Autoclave at 121° C. for 40 minutes. Just prior to use, add 10 ml of 1M $NaHCO_3$ pH 9 per 100 ml medium.

Fermentation Procedure

The fungal strains were maintained on agar in petri dishes (9 cm) or on slants with PDA, YPG or MEA (see list of media). 1 agar slant was washed off with 10 ml sterile distilled water and 3 ml were used to inoculate 1 shake flask.

The fungal strains were grown in shake flasks under the following growth conditions:
media: A and B (see list of media)
Temperature: 26° C.
RPM:
    A: stationary
    B: 125–200
Incubation time:
    A: 6 to 30 days
    B: 2–21 days.

The bacterial isolate was maintained on agar slopes with TY agar pH 9 which consists of:
20 g tryptone, 5 g yeast extract, 0.7 ml of a 1% solution of $FeCl_2. 4H_2O$, 0.1 ml of a 1% solution of $MnCl_2. 4H_2O$, 1.5 ml of a 1% solution of $MgSO_4. 7H_2O$, 20 g agar and deionized water up to 1000 ml. Autoclave at 121° C. for 20 minutes. Before pouring the plates, add 10 ml of sterile 1M $NaHCO_3$ pH9 to 100 ml agar.

The slants were incubated at 30° C. for 4 days. 1 slant was washed off with 10 ml sterile distilled water and 3 ml were used to inoculate each flask.

The bacterium was grown in shake flasks containing Medium C at 30° C. for 4 days at 300 rpm.

Activity Test

The culture broths which were produced in B and C, were centrifuged at 10,000 rpm for 10 minutes. The supernatants were tested for XET activity.

To each flask with wheat bran and fully grown culture, was added 200 ml tap water and shaken at 200 rpm for 2 hours. The culture broth was then centrifuged and the supernatant tested for XET.

XET Analysis

The samples were analysed using the "dot-blot" assay described above.

Results

Using the method described above, 1 Bacillus sp and several fungi belonging to different taxonomical groups were found to be positive. The results are shown in the table below.

The *Bacillus alcalophilus* was positive when grown on Medium C pH 9 (see list of media) for 4 days at 30° C. at 300 rpm.

| Fungal Isolate | Medium A | Medium B |
|---|---|---|
| *Actinomucor elegans* | + | − |
| *Dichotomocladium hesseltinei* | + | + |
| *Gongronella butleri* | not done | + |
| *Mucor miehei* var minor | + | + |
| *Sporodiniella umbellata* | − | + |
| *Alternaria sp* | + | − |
| *Aposphaeria* | not done | + |
| *Aspergillus tamarii* | + | + |
| *Botrytis cinerea* | + | + |
| *Chaetapiospora rhododendri* | − | + |
| *Colletotrichum aculatum* | + | − |
| *Colletotrichum crassipes* | + | − |
| *Coniothyrium dunkii* | + | + |
| *Coniothyrium olivaceoum* | + | − |
| *Coniothyrium sp* | − | + |
| *Coryneum castaneicola* | − | + |
| *Cytospora spp* | + | + |
| *Diplodia gossypina* | + | + |
| *Discula sp* | + | + |
| *Embellisia hyacinthi* | + | − |
| *Eupenicillium javanicum* | + | − |
| *Eurotium chevalieri* | − | + |
| *Fusarium solani* | + | − |
| *Galiella celebica* | + | + |
| *Lulworthia uniseptata* | + | + |
| *Nodulisporium sp* | + | − |
| *Oedocephalum sp* | − | + |
| *Penicillium canescens* | + | − |
| *P. capsulatum* | + | − |
| *P. italicum* | not done | + |
| *P. olsonii* | + | − |
| *P. pinophilum* | + | not done |
| *P. roqueforti* | + | + |
| *P. verruculosum* | + | + |
| *Pestalotia sp* | not done | + |
| *Pestalotiopsis sp* | + | + |
| *Petromyces alliaceus* | + | + |
| *Phoma neoloba* | + | − |
| *Phoma tropica* | + | + |
| *Phomopsis cirsii* | − | + |
| *Phomopsis ilicis* | + | + |
| *Phyllosticta sp* | + | − |
| *Plowrightia ribesia* | + | + |
| *Poronia punctata* | + | + |
| *Pseudoplectania nigrella* | + | + |
| *Pyronema domesticum* | + | + |
| *Ramularia sp* | + | − |
| *Seimatosporium lichenicola* | + | − |
| *Septoria sp* | + | not done |
| *Talaromyces flavus* | + | + |
| *Tubeufia amazonensis* | + | − |
| *Tiarosporella phaseolina* | + | + |
| *Tiarosporella sp* | − | + |
| *Verticillium sp* | + | + |
| *Volutella buxi* | + | − |
| *Xylaria sp* | + | + |
| *Corticium roseum* | + | − |
| *Schizophyllum sp* | + | + |
| *Stereum hirsutum* | + | − |
| *Trametes hirsuta* | + | + |
| *Tubulicrinis subulatus* | + | + |
| *Acrodontium crateriforme* | + | − |
| *Aureobasidium pullulans* | + | − |
| *Circinotrichum sp* | − | + |
| *Cryptocline sp* | + | − |
| *Ellisiopsis sp* | + | − |
| *Epicoccum nigrum* | − | + |
| *Gliocladium sp* | + | − |
| *Helicorhoidion irregulare* | + | − |
| *Hendersonia spp* | + | + |
| *Mariannaea sp* | + | − |
| *Microsphaeropsis sp* | + | − |
| *Ramularia sp* | + | − |
| *Sarcopodium sp* | + | − |

-continued

| Fungal Isolate | Medium A | Medium B |
|---|---|---|
| Spadicoides sp | − | + |
| Speiropsis pedatospora | + | − |
| Sporotrichum exile | + | + |
| Stilbella sp | + | − |
| Trichothecium sp | + | + |
| Trimmatostroma abietes | + | + |
| Tubakia dryina | + | + |
| Wiesneriomyces sp | + | − |
| Zygosporium masonii | + | + |
| Vialaea | + | not done |

+ = positive
− = negative

EXAMPLE 2
Purification and Characterization of *Dichotomocladium hesseltinei* XET 15 PDA agar slopes were inoculated with *Dichotomocladium hesseltinei* (CBS 164.61) and incubated at 26° C. for 7 days. They were washed off with about 250 ml sterile distilled water with 0.1% Tween 80 and used to inoculate 80 shake flasks containing Medium B (2–3 ml/flask). The flasks were shaken at 200 rpm, 26° C. for 5 days after which time the culture broth was centrifuged at 4000 rpm for 15 minutes.

The supernatant containing xyloglucan endotransglucosylase (XET) was purified using the following method:

Filter aid was added to the culture broth which was filtered through a filtration cloth. This solution was further filtered through a Seitz depth filter plate resulting in a clear solution. The pH of the filtrate was adjusted to pH 8.0 and the filtrate was diluted with deionised water to give the same conductivity as 20 mM Tris/HCl, pH 8.0.

The XET enzyme was applied to a Q-sepharose FF column equilibrated in 20 mM Tris/HCl, pH 8.0 and the enzyme was eluted with an increasing linear NaCl gradient (0→0.5M). The XET activity eluted as a single peak. The pooled XET was transferred to 20 mM Tris/HCl, pH 8.0 on a Sephadex G25 column and rechromatographed on a Q-sepharose FF column equilibrated in 20 mM Tris/HCl, pH 8.0. The column was eluted with an increasing linear NaCl gradient (0→0.2M). XET containing fractions were pooled and $(NH_4)_2SO_4$ was added to 1.4M final concentration. A Phenyl Toyopearl 650S column was equilibrated in 1.4M $(NH_4)_2SO_4$, 10 mM succinic acid, pH 7.0 and the XET enzyme was applied to this column and eluted with a decreasing linear $(NH_4)_2SO_4$ gradient (1.4→0M). XET containing fractions were pooled and concentrated on an ultrafiltration cell with a 10 kDa cut-off regenerated cellulose membrane. The concentrated enzyme was applied to a Superdex200 size exclusion column equilibrated in 100 mM $H_3BO_3$, 10 mM dimethyl glutaric acid, 2 mM $CaCl_2$, pH 7.0. Fractions eluted from the Superdex200 column were analyzed by SDS-PAGE and pure XET fractions were pooled.

The *Dichotomocladium hesseltinei* XET migrates on SDS-PAGE as a band with $M_r$=24 kDa. N-terminal amino acid sequencing of the 24 kDa component was carried out following SDS-PAGE and electroblotting onto a PVDF-membrane. The following N-terminal amino acid sequence (SEQ ID No. 1) could be deduced:
Ala-Glu-Phe-Cys-Gly-Gln-Trp-Asp-Thr-Gln-Thr-Val-Gly-Asn-Tyr-Ile-Val-Tyr-Asn-Asn-Leu-Leu-Gly-Ala-Gly-Ser-Ala.

The present invention also relates to a microbial XET enzyme comprising the amino acid sequence shown in SEQ ID No. 1 or a XET being at least 80% homologous with the amino acid sequence SEQ ID No. 1, preferably being at least 85% homologous with SEQ ID No. 1, more preferably being at least 90% homologous with SEQ ID No.1, even more preferably being at least 95% homologous with SEQ ID No. 1, in particular being at least 98% homologous with SEQ ID No. 1.

A polypeptide is considered to be X% homologous to the parent XET if a comparison of the respective amino acid sequences, performed via known algorithms, such as the one described by Lipman and Pearson in *Science* 227, 1985, p. 1435, reveals an identity of X%.

In addition, mass spec. analysis of the *Dichotomocladium hesseltinei* XET gave a value of 23 006 Da.

EXAMPLE 3
Purification and Characterization of *Tiarosporella phaseolina* XET 15 PDA agar slopes were inoculated with *Tiarosporella phaseolina* (CBS 446.97) and incubated at 26° C. for 7 days. They were washed off with about 250 ml sterile distilled water with 0.1 Tween 80 and used to inoculate 80 shake flasks containing Medium B (2–3 ml/flask). The flasks were shaken at 200 rpm, 26° C. for 7 days after which time the culture broth was centrifuged at 4000 rpm for 15 minutes.

The supernatant containing xyloglucan endotransglucosylase (XET) was purified using the following method:

Filter aid was added to the culture broth which was filtered through a filtration cloth. This solution was further filtered through a Seitz depth filter plate resulting in a clear solution. The filtrate was concentrated by ultrafiltration on 3 kDa cut-off polyethersulfone membranes followed by dialfiltration with distilled water to reduce the conductivity. The pH of the concentrated enzyme was adjusted to pH 5.0. The conductivity of the concentrated enzyme was 1.7 mS/cm.

The XET enzyme was applied to a S-sepharose FF column equilibrated in 20 mM $CH_3COOH/NaOH$, pH 5.0 and the enzyme was eluted with an increasing linear NaCl gradient (0→0.5M). The XET activity eluted as a single peak. The pooled XET was transferred to 20 mM $CH_3COOH/NaOH$, pH 4.0 by dialysis. The dialysed enzyme was applied to a SOURCE 30S column equilibrated in 20 mM $CH_3COOH/NaOH$, pH 4.0. After washing the column the XET activity was eluted with an increasing linear NaCl gradient (0→0.5M). Fractions with XET activity were pooled and dialysed against 20 mM Tris/HCl, pH 8.0. The dialysed enzyme was applied to a SOURCE 30Q column equilibrated in 20 mM Tris/HCl, pH 8.0. After washing the column the XET activity was eluted with an increasing linear NaCl gradient (0→0.5M). Fractions with XET activity were pooled and concentrated on an ultrafiltration cell with a 10 kDa cut-off regenerated cellulose membrane. The concentrated enzyme was applied to a Superdex200 size exclusion column equilibrated in 100 mM $H_3BO_3$, 10 mM dimethyl glutaric acid, 2mM $CaCl_2$, pH 7.0. Fractions eluted from the Superdex200 column were analyzed by SDS-PAGE and pure XET fractions were pooled.

The *Tiarosporella phaseolina* XET migrates on SDS-PAGE as a band with $M_r$=24 kDa. N-terminal amino acid sequencing of the 24 kDa component was carried out following SDS-PAGE and electroblotting onto a PVDF-membrane. The following N-terminal amino acid sequence (SEQ. ID No. 2) could be deduced:
Xaa-Asp-Phe-Cys-Gly-Gln-Trp-Asp-Asn-Val-Lys-Asn-Gly-Pro-Tyr-Thr-Leu-Tyr-Asn-Asn-Leu-Gly-Gly-Lys The present invention also relates to a microbial XET enzyme comprising the amino acid sequence shown in SEQ ID No. 2 or a XET being at least 80% homologous with the amino acid sequence SEQ ID No. 2, preferably being at least 85% homologous with SEQ ID No. 2, more preferably being at least 90% homologous with SEQ ID No. 2, even more preferably being at least 95% homologous with SEQ ID No. 2, in particular being at least 98% homologous with SEQ ID No. 2.

A polypeptide is considered to be X% homologous to the parent XET if a comparison of the respective amino acid sequences, performed via known algorithms, such as the one described by Lipman and Pearson in *Science* 227, 1985, p. 1435, reveals an identity of X%.

EXAMPLE 4
Purification and Characterization of *Pseudoplectania nigrella* XET 15 PDA agar slopes were inoculated with *Pseudoplectania nigrella* (CBS 444.97) and incubated at 26° C. for 7 days. They were washed off with about 250 ml sterile distilled water with 0.1% Tween 80 and used to inoculated 80 shake flasks containing Medium B (2–3 ml/flask). The flasks were shaken at 200 rpm, 26° C. for 7 days after which time the culture broth was centrifuged at 4000 rpm for 15 minutes.

The supernatant containing xyloglucan endotransglycosylase (XET) was purified using the following method:

Filter aid was added to the culture broth which was filtered through a filtration cloth. This solution was further filtered through a Seitz depth filter plate resulting in a clear solution. The pH of the filtrate was adjusted to pH 5.0 and the filtrate was diluted with deionised water to give the same conductivity as 20 mM $CH_3COOH$/NaOH, pH 5.0.

The XET enzyme was applied to a S-sepharose FF column equilibrated in 20 mM $CH_3COOH$/NaOH, pH 5.0 and the enzyme was eluted with an increasing linear NaCl gradient (0→0.25M). The XET activity eluted as a single peak. The pooled XET was transferred to 20 mM Hepes/NaOH, pH 7.0 on a Sephadex G25 column and applied to a Q-sepharose FF column equilibrated in 20 mM Hepes/NaOH, pH 7.0. The column was eluted with an increasing linear NaCl gradient (0→0.5M). XET containing fractions were pooled and transferred to 20 mM $CH_3COOH$/NaOH, pH 5.0 by dialysis. A SOURCE 15S column was equilibrated in 20 mM $CH_3COOH$/NaOH, pH 5.0, and the dialysed enzyme was applied. After washing the column the XET enzyme was eluted with an increasing linear NaCl gradient (0→0.2M). XET containing fractions were pooled and concentrated on an ultrafiltration cell with a 10 kDa cut-off regenerated cellulose membrane. The concentrated enzyme was applied to a Superdex200 size exclusion column equilibrated in 20 mM $CH_3COOH$/NaOH, 100 mM NaCl, pH 5.0. Fractions eluted from the Superdex200 column were analyzed by SDS-PAGE and pure XET fractions were pooled.

The *Pseudoplectania nigrella* XET migrates on SDS-PAGE as a band with $M_r$=58 kDa. Following SDS-PAGE and electroblotting onto a PVDF-membrane it was found that the 58 kDa component had a blocked N-terminus.

A highly purified preparation of *Pseudoplectania nigrella* XET was reduced and alkylated. A sample of the enzyme was then degraded with Lys-C. Peptides were isolated by RP-HPLC on a long Vydac C18 in a SMART system using TFA/AN and repurified in TFA/isopropanol. Selected peptides were analyzed by Edman degradation.

In Table 1 the sequences obtained from 8 peptides are shown. Two peptides were found to be homologous to glucanase- and xylanase-like enzymes but the majority did not show any or only irrelevant homology to known sequences.

TABLE 1

Sequence of Lys-C peptides from *P. nigrella* XET

| Peptide | Run no. | Sequence | Comments on homology |
|---|---|---|---|
| XET lysyl 070198-2fr5 | 3777 | WNDPVVK | Homology to *B. subtilis* lysis protein |
| XET lysyl 080198-4fr3 | 3778 | (S/Y)RFNAPALIGE[WQ] | Nothing found |
| XET lysyl 090198-1fr6 | 3779 | LIFE | Too small |
| XET lysyl 070198-1fr5 | P379 | EDGSYLKYAK | irrelevant homologies |
| XET lysyl 070198-1fr3 | P380 | EWGTTGKFNK | Homology to endoglucanase |
| XET lysyl 080198-1fr1 | P381 | KVTAVEAWK | Weak homology to xyn1_asptu. Endoxylanase |
| XET lysyl 080198-2fr1 | P382 | XFYQIANS(Q/I) | Nothing found |
| XET lysyl 080198-3fr1 | P383 | AALXXVMK | Nothing found |

EXAMPLE 5
pH Profile of *Dichotomocladium hesseltinei, Tiarosporella phaseolina* and *Pseudoplectania nigrella* XET and Xyloglucanase The xyloglucan endotransglycosylase of *Dichotomocladium hesseltinei, Tiarosporella phaseolina* and *Pseudoplectania nigrella* were checked for their pH profile. The pure enzymes were diluted in buffers ranging from pH 3.0 to 11.0 so that in the final dilution, the protein concentration was the same i.e. $A_{280}$=0.004. The samples were then assayed for XET using the XET-dot-blot-assay (described earlier). The fluorescent spots were judged visually and graded from 0–10. The units used in FIG. 1 are therefore arbitrary units.

Figure 1:
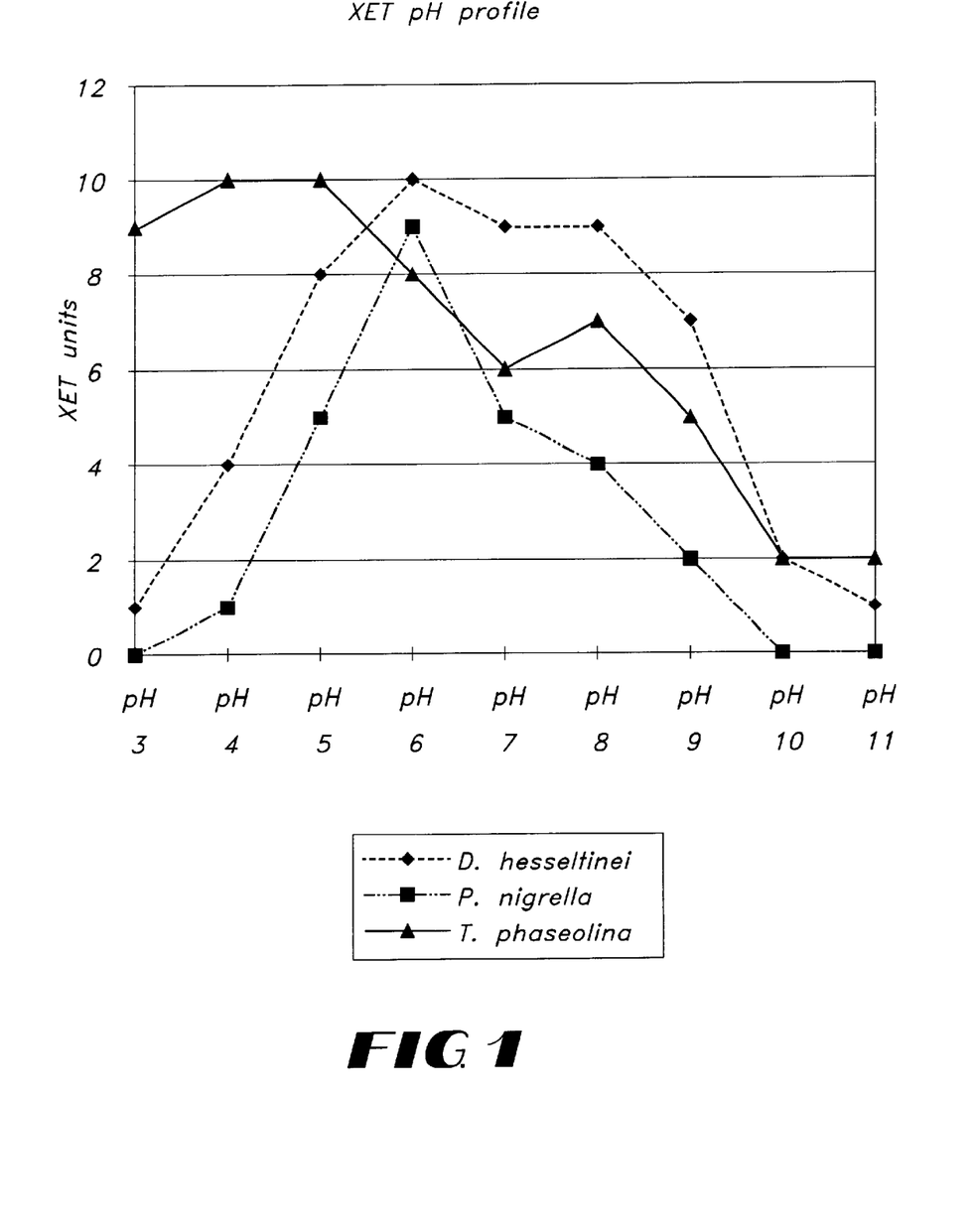
FIG. 1 shows the pH profiles of *Dichotomocladium hesseltinei, Tiarosporella phaseolina* and *Pseudoplectania nigrella* XET activity (Δ:*Tiarosporella phaseolina*; □:*Pseudoplectania nigrella*; and ♦:*Dichotomocladium hesseltinei*) obtained according to Example 5.

It can be seen from FIG. 1 that the XET is active between pH 3 and pH 11, in particular between pH 4 and pH 9.

All the isolates with XET activity were also tested for xyloglucanase activity. The ratio between the 2 enzymes varies from isolate to isolate. The enzymes were diluted in the same buffers as for the XET pH profile activity until the final protein concentration was the same and assayed for xyloglucanase activity. AZCL xyloglucan was used. The xyloglucanase method used was the following:

Substrate: 0.4% AZCL-xyloglucan suspended in demineralised water.
Buffer: 100 mM $H_3BO_3$, 10 mM Dimethy glutaric acid, 2 mM $CaCl_2$, pH 7.
Analysis:

An Eppendorf thermomixer is switched on at 40° C.

500 μl 0.4% AZCL-xyloglucan is mixed with 500 μl buffer and put on ice.

20 μl enzyme is added and incubated in the Eppendorf thermomixer until a suitable colour is reached.

The samples are returned to the ice bath to prevent further reaction while the samples are centrifuged at 0° C.

200 μl samples are transferred to micro titre plates and the blue colour is measured at 650 nm.

Figure 2:
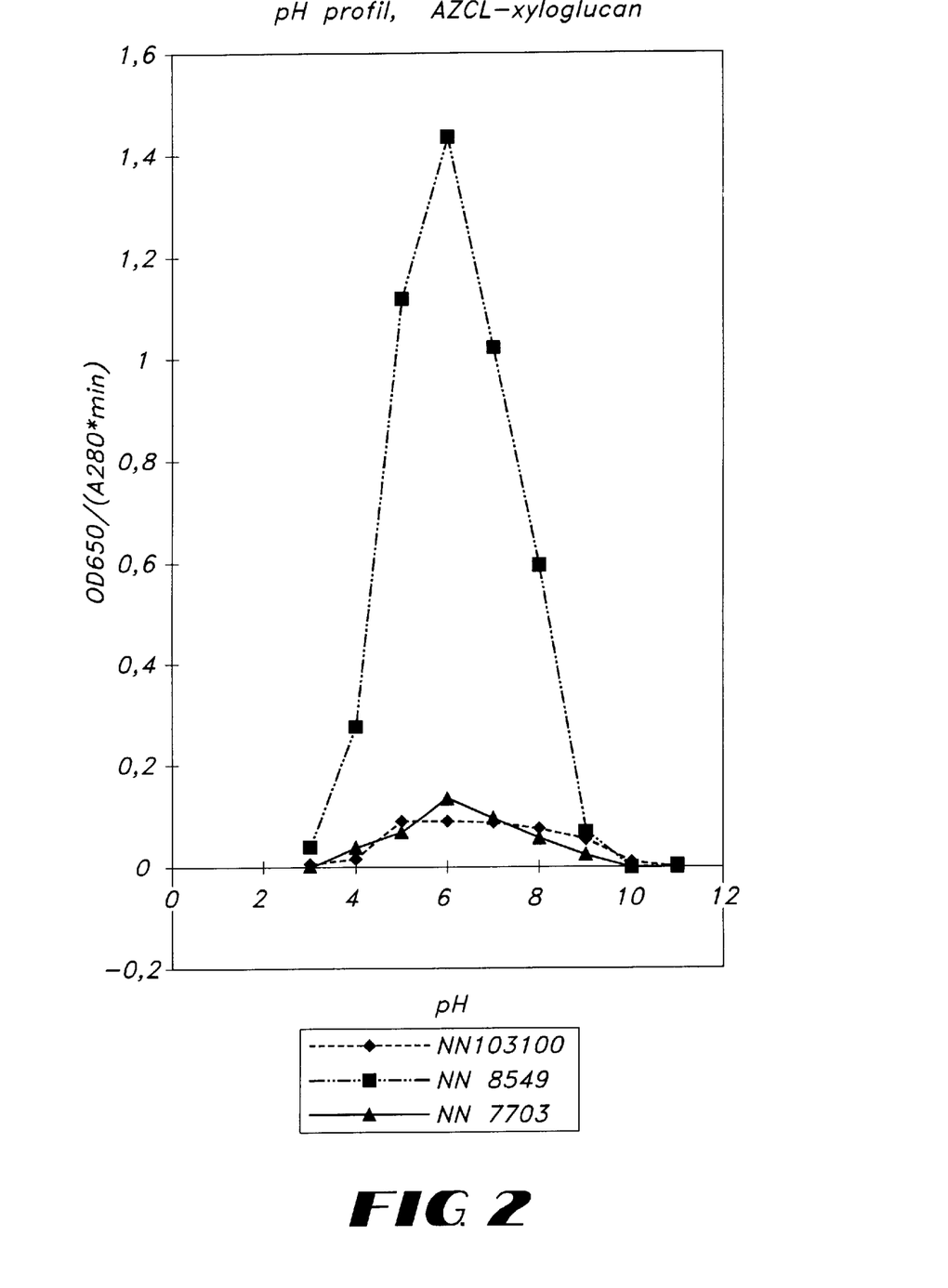
FIG. 2 shows the pH profiles of *Dichotomocladium hesseltinei, Tiarosporella phaseolina* and *Pseudoplectania nigrella* xyloglucanase activity (Δ:*Tiarosporella phaseolina*; □:*Pseudoplectania nigrella*; and ♦:*Dichotomocladium hesseltinei*) obtained according to Example 5.

The results are shown in FIG. 2.

EXAMPLE 6
Cloning and Expression of a Xyloglucan Endotransglycosylase Enzyme (XET) from *Tiarosporella phaseolina* CBS No. 446.97

Deposited Organisms
*Tiarosporella phaseolina* CBS No. 446.97.
Other Strains

Yeast strain: The *Saccharomyces cerevisiae* strain used was W3124 (van den Hazel, H. B; Kielland-Brandt, M. C.; Winther, J. R. in *Eur. J. Biochem.*, 207, 277–283, 1992; (MATa; ura 3–52; leu 2–3, 112; his 3-D200; pep 4–1137; prc1::HIS3; prb1::LEU2; cir+). *E. coli* strain: DH10B (Life Technologies)

Plasmids

The Aspergillus expression vector pHD414 is a derivative of the plasmid p775 (described in EP 238 023). The construction of pHD414 is further described in WO 93/11249. pYES 2.0 (Invitrogen)

Media

YPD:

10 g yeast extract, 20 g peptone, $H_2O$ to 900 ml. Autoclaved, 100 ml 20% glucose (sterile filtered) added.

YPM:

10 g yeast extract, 20 g peptone, $H_2O$ to 900 ml. Autoclaved, 100 ml 20% maltodextrin (sterile filtered) added.

10×Basal salt:

75 g yeast nitrogen base, 113 g succinic acid, 68 g NaOH, $H_2O$ ad 1000 ml, sterile filtered.

SC-URA:

100 ml 10× Basal salt, 28 ml 20% casamino acids without vitamins, 10 ml 1% tryptophan, $H_2O$ ad 900 ml, autoclaved, 3.6 ml 5% threonine and 100 ml 20% glucose or 20% galactose added.

SC-agar:

SC-URA, 20 g/l agar added. AZCL Xyloglucan (Megazyme, Australia)

Expression Cloning in Yeast

Expression cloning in yeast was done as described by H. Dalboege et al. (H. Dalboege et al Mol. Gen. Genet (1994) 243:253–260.; WO 93/11249; WO 94/14953), which are hereby incorporated as reference. All individual steps of Extraction of total RNA, cDNA synthesis, Mung bean nuclease treatment, Blunt-ending with T4 DNA polymerase, and Construction of libraries was done according to the references mentioned above.

Fermentation Procedure of *Tiarosporella phaseolina* CBS No. 446.97 for mRNA Isolation

*Tiarosporella phaseolina* CBS No. 446.97 was inoculated from a plate with outgrown mycelium into a shake flask containing 100 ml medium B (see media). The culture was incubated at 26° C. and 200 rpm for 7 days. The resulting culture broth was filtered through miracloth and the mycelium was frozen down in liquid nitrogen.

mRNA was isolated from mycelium from this culture as described in (H. Dalboege et al Mol. Gen. Genet (1994) 243:253–260.; WO 93/11249; WO 94/14953).

Extraction of total RNA was performed with guanidinium thiocyanate followed by ultracentrifugation through a 5.7 M CsCl cushion, and isolation of poly(A)+ RNA was carried out by oligo(dT)-cellulose affinity chromatography using the procedures described in Wo 94/14953.

cDNA Synthesis

Double-stranded cDNA was synthesized from 5 mg poly (A)+ RNA by the RNase H method (Gubler and Hoffman (1983) Gene 25:263–269, Sambrook et al. (1989) Molecular cloning: A laboratory manual, Cold Spring Harbor lab., Cold Spring Harbor, N.Y.). The poly(A)+ RNA (5 µg in 5 µl of DEPC-treated water) was heated at 70° C. for 8 min. in a pre-siliconized, RNase-free Eppendorph tube, quenched on ice and combined in a final volume of 50 µl with reverse transcriptase buffer (50 mM Tris-Cl, pH 8.3, 75 mM KCl, 3 mM $MgCl_2$, 10 mM DTT, Bethesda Research Laboratories) containing 1 mM of DATP, dGTP and dTTP and 0.5 mM 5-methyl-dCTP (Pharmacia), 40 units human placental ribonuclease inhibitor (RNasin, Promega), 1.45 µg of oligo(dT)$_{18}$-Not I primer (Pharmacia) and 1000 units SuperScript II RNase H reverse transcriptase (Bethesda Research Laboratories). First-strand cDNA was synthesized by incubating the reaction mixture at 45° C. for 1 hour. After synthesis, the mRNA:cDNA hybrid mixture was gelfiltrated through a MicroSpin S-400 HR (Pharmacia) spin column according to the manufacturer's instructions.

After the gelfiltration, the hybrids were diluted in 250 µl second strand buffer (20 mM Tris-Cl, pH 7.4, 90 mM KCl, 4.6 mM $MgCl_2$, 10 mM $(NH_4)_2SO_4$, 0.16 mM bNAD+) containing 200 µl of each dNTP, 60 units *E. coli* DNA polymerase I (Pharmacia), 5.25 units RNase H (Promega) and 15 units *E. coli* DNA ligase (Boehringer Mannheim). Second strand cDNA synthesis was performed by incubating the reaction tube at 16° C. for 2 hours and additional 15 min. at 25° C. The reaction was stopped by addition of EDTA to a final concentration of 20 mM followed by phenol and chloroform extractions.

Mung Bean Nuclease Treatment

The double-stranded cDNA was precipitated at −20° C. for 12 hours by addition of 2 vols 96% EtOH, 0.2 vol 10M $NH_4Ac$, recovered by centrifugation, washed in 70% EtOH, dried and resuspended in 30 µl Mung bean nuclease buffer (30 mM NaAc, pH 4.6, 300 mM NaCl, 1 mM $ZnSO_4$, 0.35 mM DTT, 2% glycerol) containing 25 units Mung bean nuclease (Pharmacia). The single-stranded hair-pin DNA was clipped by incubating the reaction at 30° C. for 30 min., followed by addition of 70 µl 10 mM Tris-Cl, pH 7.5, 1 mM EDTA, phenol extraction and precipitation with 2 vols of 96% EtOH and 0.1 vol 3M NaAc, pH 5.2 on ice for 30 min.

Blunt-Ending with T4 DNA Polymerase

The double-stranded cDNAs were recovered by centrifugation and blunt-ended in 30 ml T4 DNA polymerase buffer (20 mM Tris-acetate, pH 7.9, 10 mM MgAc, 50 mM KAc, 1 mM DTT) containing 0.5 mM of each dNTP and 5 units T4 DNA polymerase (New England Biolabs) by incubating the reaction mixture at 16° C. for 1 hour. The reaction was stopped by addition of EDTA to a final concentration of 20 mM, followed by phenol and chloroform extractions, and precipitation for 12 hours at −20° C. by adding 2 vols 96% EtOH and 0.1 vol 3M NaAc pH 5.2.

Adaptor Ligation, Not I Digestion and Size Selection

After the fill-in reaction the cDNAs were recovered by centrifugation, washed in 70% EtOH and dried. The cDNA pellet was resuspended in 25 µl ligation buffer (30 mM Tris-Cl, pH 7.8, 10 mM $MgCl_2$, 10 mM DTT, 0.5 mM ATP) containing 2.5 µg non-palindromic BstXI adaptors (Invitrogen) and 30 units T4 ligase (Promega) and incubated at 16° C. for 12 hours. The reaction was stopped by heating at 65° C. for 20 min. and then cooling on ice for 5 min. The adapted cDNA was digested with Not I restriction enzyme by addition of 20 λl water, 5 µl 10×Not I restriction enzyme buffer (New England Biolabs) and 50 units Not I (New England Biolabs), followed by incubation for 2.5 hours at 37° C. The reaction was stopped by heating at 65° C. for 10 min. The cDNAs were size-fractionated by gel electrophoresis on a 0.8% SeaPlaque GTG low melting temperature agarose gel (FMC) in 1×TBE to separate unligated adaptors and small cDNAs. The cDNAs were size-selected with a cut-off at 0.7 kb and rescued from the gel by use of b-Agarase (New England Biolabs) according to the manufacturer's instructions and precipitated for 12 hours at −20° C. by adding 2 vols 96% EtOH and 0.1 vol 3M NaAc pH 5.2.

Construction of Library

The directional, size-selected cDNAs were recovered by centrifugation, washed in 70% EtOH, dried and resuspended in 30 μl 10 mM Tris-Cl, pH 7.5, 1 mM EDTA. The cDNAs were desalted by gelfiltration through a MicroSpin S-300 HR (Pharmacia) spin column according to the manufacturer's instructions. Three test ligations were carried out in 10 μl ligation buffer (30 mM Tris-Cl, pH 7.8, 10 mM MgCl$_2$, 10 mM DTT, 0.5 mM ATP) containing 5 μl double-stranded cDNA (reaction tubes #1 and #2), 15 units T4 ligase (Promega) and 30 ng (tube #1), 40 ng (tube #2) and 40 ng (tube #3, the vector background control) of BstXI-NotI cleaved pYES 2.0 vector. The ligation reactions were performed by incubation at 16° C. for 12 hours, heating at 70° C. for 20 min. and addition of 10 μl water to each tube. 1 μl of each ligation mixture was electroporated into 40 μl electrocompetent *E. coli* DH10B cells (Bethesda research Laboratories) as described (Sambrook et al. (1989) Molecular cloning: A laboratory manual, Cold Spring Harbor lab., Cold Spring Harbor, N.Y.). Using the optimal conditions a library was established in *E. coli* consisting of pools. Each pool was made by spreading transformed *E. coli* on LB+ampicillin agar plates giving 15,000–30,000 colonies/plate after incubation at 37° C. for 24 hours. 20 ml LB+ampicillin was added to the plate and the cells were suspended herein. The cell suspension was shaked in a 50 ml tube for 1 hour at 37° C. Plasmid DNA was isolated from the cells according to the manufacturer's instructions using QIAGEN plasmid kit and stored at −20° C.

1 μl aliquots of purified plasmid DNA (100 ng/ml) from individual pools were transformed into *S. cerevisiae* W3124 by electroporation (Becker and Guarante (1991) Methods Enzymol. 194:182–187) and the transformants were plated on SC agar containing 2% glucose and incubated at 30° C.

Identification of Positive Colonies

Colonies were screened indirectly for XET by finding xyloglucanase positive colonies.

After 3–5 days of growth, the agar plates were replica plated onto a set of SC-URA agar (with 20% galactose added) plates containing 0.1% AZCL Xyloglucan. These plates were incubated for 3–7 days at 30° C. Xyloglanase positive colonies were identified as colonies surrounded by a blue halo.

Cells from enzyme-positive colonies were spread for single colony isolation on agar, and an enzyme-producing single colony was selected for each of the Xyloglucanase-producing colonies identified.

All xyloglucanase positive colonies were tested for XET and were found to be positive.

Isolation of a cDNA Gene for Expression in Aspergillus

An XET-producing yeast colony was inoculated into 20 ml YPD broth in a 50 ml glass test tube. The tube was shaken for 2 days at 30° C. The cells were harvested by centrifugation for 10 min. at 3000 rpm.

DNA was isolated according to WO 94/14953 and dissolved in 50 ml water. The DNA was transformed into *E. coli* by standard procedures. Plasmid DNA was isolated from *E. coli* using standard procedures, and analyzed by restriction enzyme analysis. The cDNA insert was excised using the restriction enzymes BamH I and Xba I and ligated into the Aspergillus expression vector pHD414 resulting in the plasmid pA2XG80.

The cDNA inset of Qiagen purified plasmid DNA of pA2XG80 (Qiagen, USA) was sequenced with the Taq deoxy terminal cycle sequencing kit (Perkin Elmer, USA) and synthetic oligonucleotide primers using an Applied Biosystems ABI PRISM™ 377 DNA Sequencer according to the manufacturers instructions.

Transformation of *Aspergillus oryzae* or *Aspergillus niger*

Protoplasts are prepared as described in WO 95/02043, p. 16, line 21—page 17, line 12, which is hereby incorporated by reference.

100 μl of protoplast suspension is mixed with 5–25 μg of the appropriate DNA in 10 μl of STC (1.2M sorbitol, 10 mM Tris-HCl, pH=7.5, 10 mM CaCl$_2$). Protoplasts are mixed with p3SR2 (an *A. nidulans* amdS gene carrying plasmid) (Tove Christensen et al. Bio/Technology, pp 1419–1422 vol.6, Dec. 1988). The mixture is left at room temperature for 25 minutes. 0.2 ml of 60% PEG 4000 (BDH 29576), 10 mM CaCl$_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on minimal plates (Cove, Biochem. Biophys. Acta 113 (1966) 51–56) containing 1.0M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of *A. oryzae* Transformants

Each of the *A. oryzae* transformants is inoculated in 10 ml of YPM (cf. below) and propagated. After 2–5 days of incubation at 30° C., the supernatant is removed.

The XET activity is identified by using the XET dot-blot assay described earlier.

The following sequence (SEQ ID No. 3) is the cDNA insert in pYES2.0 of XG80 (XET from *Tiarosporella phaseolina*) including the BamH I and Not I recognition sites used for cloning:

GGATCCGAATTCCAACTATCCTGCCCTCCTTT-
CAAGCGAACACCATGAAGTTCTCCTCG-
GCTCTGTTTCTGGCCGCTACG

GCGGTCTTGGCTTCCGCCGCGCCGCTTGAGCGCC-
GCGCCGACTTTTGTGGTCAATGGGACAACG-
TGAAGAACGGACCTTA

CACTCTTTACAACAACCTGTGGGGAAAA-
GATGCTTCCGGAGCCTCCGGATCGCAAT-
GCACCGGCGTCGATAGCTTCAGCA

GCAACACCATCGCTTGGCACACATCCTG-
GTCCTGGTCCGGTGCTCAGTACAATGT-
CAAGTCTTACGCAAACGTGGTCGTC

GACATCACCTCTAAGAAACTCAGCGCCATCAG-
CAGCATTAACAGCATCTGGCGCTGGGCT-
TACACGGGTAGCAACATTGT

TGCCAATGTTGCCTACGATATCTTCACTTCAT-
CCACTGTCGGTGGTAGCGAGGAATATGAAA-
TCATGATATGGGTTGGTG

CTCTCGGTGGTGCTGGTCCGATCTCATCTACC-
GGCTCCCCTATTGCCACCGTTTCCCTTG-
CAGGCTCCTCGTGGAAGCTC

TACAAAGGGCCCAACGGGCAGATGACCGTGTT-
CAGCTTCGTCGCCGAGTCCAACGTGAA-
CAACTTCAGCGGTGACCTTAA

CGCTTTCATCAAGTACCTCACCGGCAACCAGGG-
CCTTCCCGCCTCGCAATACATCAAGAG-
CATTGGCGCTGGCACTGAGC

CGTTCACGGGTTCCAACGCCAAGCTGACCACTTC-
CTCCTACACTGTCAGCTTCAGATAACTGTGAA-
GCTTTATGCTGCCC

TTATGCATCATCCTTGTACATAGTTATCACCAGGG-
GACTCTTGTAAATACGATTGCCTTATTAACCG-
CCTGCATCTGCTT

TCACACAATGGCATTTACCAATCAACAGTGCG-
CCTCGAATCCGTAAAAGGTGGCTTAAAAA-
AAAAATTCCTGCGGCCGC.

The following sequence (SEQ ID no. 4) is the amino acid sequence of the coding region of XG80:

MKFSSALFLAATAVLASAAPLERRADFCGQW-
DNVKNGPYTLYNNLWGKDASGASGSQCT-
GVDSFSSNTIAWHTSWSWSGA
QYNVKSYANVVVDITSKKLSAISSINSIWRWAYTG-
SNIVANVAYDIFTSSTVGGSEEYEIMIWVGALGG-
AGPISSTGSPI
ATVSLAGSSWKLYKGPNGQMTVFSFVAESNVNN-
FSGDLNAFIKYLTGNQGLPASQYIKSIGAGTEP-
FTGSNAKLTTSSYT
VSFR.

The present invention also relates to a microbial XET enzyme comprising the amino acid sequence shown in SEQ ID No. 4 or a XET being at least 80% homologous with the amino acid sequence SEQ ID No. 4, preferably being at least 85% homologous with SEQ ID No. 4, more preferably being at least 90% homologous with SEQ ID No. 4, even more preferably being at least 95% homologous with SEQ ID No. 4, in particular being at least 98% homologous with SEQ ID No. 4.

A polypeptide is considered to be X% homologous to the parent XET if a comparison of the respective amino acid sequences, performed via known algorithms, such as the one described by Lipman and Pearson in *Science* 227, 1985, p. 1435, reveals an identity of X%.

A clone C1.XG80 was deposited at DSMZ on 24 February 1998 under Accession No. DSM 12032.

What is claimed is:

1. A method for the production of a fungal xyloglucan endotransglycosylase enzyme (XET), comprising:
(a) culturing in a suitable nutrient medium a fungus expressing a fungal XET under conditions conducive to the production of the XET, wherein the XET comprises an amino acid sequence selected from the group consisting of:
the amino acid sequence of SEQ ID NO:1;
the amino acid sequence of SEQ ID NO:2;
the amino acid sequence of SEQ ID NO:4; and
an amino acid sequence having at least 80% homology with the amino acid sequence of SEQ ID NO:1, SEQ ID NO:2 or SEQ ID NO:4, and exhibiting XET enzyme activity; and
(b) recovering the XET from the nutrient medium.

2. The method of claim 1, wherein the XET comprises the amino acid sequence of SEQ ID NO:1.

3. The method of claim 1, wherein the XET comprises the amino acid sequence of SEQ ID NO:2.

4. The method of claim 1, wherein the XET comprises the amino acid sequence of SEQ ID NO:4.

5. The method of claim 1, wherein the XET comprises an amino acid sequence having at least 80% homology with the amino acid sequence of SEQ ID NO:1.

6. The method of claim 1, wherein the XET comprises an amino acid sequence having at least 80% homology with the amino acid sequence of SEQ ID NO:2.

7. The method of claim 1, wherein the XET comprises an amino acid sequence having at least 80% homology with the amino acid sequence of SEQ ID NO:4.

8. A method for the production of a fungal xyloglucan endotransglycosylase enzyme (XET), comprising:
(a) culturing in a suitable nutrient medium a fungus expressing a fungal XET under conditions conducive to the production of the XET, wherein the XET comprises an amino acid sequence having at least 80% homology with the amino acid sequence of SEQ ID NO:1, and wherein said XET exhibits XET enzyme activity; and
(b) recovering the XET from the nutrient medium.

9. The method of claim 8, wherein the XET comprises an amino acid sequence having at least 85% homology with the amino acid sequence of SEQ ID NO:1.

10. The method of claim 8, wherein the XET comprises an amino acid sequence having at least 90% homology with the amino acid sequence of SEQ ID NO:1.

11. The method of claim 8, wherein the XET comprises an amino acid sequence having at least 95% homology with the amino add sequence of SEQ ID NO:1.

12. The method of claim 8, wherein the XET comprises an amino acid sequence having at least 98% homology with the amino acid sequence of SEQ ID NO:1.

13. A method for the production of a fungal xyloglucan endotransglycosylase enzyme XET), comprising:
(a) culturing in a suitable nutrient medium a fungus expressing a fungal XET under conditions conducive to the production of the XET, wherein the XET comprises an amino acid sequence having at least 80% homology with the amino acid sequence of SEQ ID NO:2, and wherein said XET exhibits XET enzyme activity; and
(b) recovering the XET from the nutrient medium.

14. The method of claim 13, wherein the XET comprises an amino acid sequence having at least 85% homology with the amino acid sequence of SEQ ID NO:2.

15. The method of claim 13, wherein the XET comprises an amino add sequence having at least 90% homology with the amino acid sequence of SEQ ID NO:2.

16. The method of claim 13, wherein the XET comprises an amino acid sequence having at least 95% homology with the amino acid sequence of SEQ ID NO:2.

17. The method of claim 13, wherein the XET comprises an amino acid sequence having at least 98% homology with the amino acid sequence of SEQ ID NO:2.

18. A method for the production of a fungal xyloglucan endotransglycosylase enzyme (XET), comprising:
(a) culturing in a suitable nutrient medium a fungus expressing a fungal XET under conditions conducive to the production of the XET, wherein the XET comprises an amino acid sequence having at least 80% homology with the amino acid sequence of SEQ ID NO:4, and wherein said XET exhibits XET enzyme activity; and
(b) recovering the XET from the nutrient medium.

19. The method of claim 18, wherein the XET comprises an amino acid sequence having at least 85% homology with the amino acid sequence of SEQ ID NO:4.

20. The method of claim 18, wherein the XET comprises an amino acid sequence having at least 90% homology with the amino acid sequence of SEQ ID NO:4.

21. The method of claim 18, wherein the XET comprises an amino acid sequence having at least 95% homology with the amino acid sequence of SEQ ID NO:4.

22. The method of claim 18, wherein the XET comprises an amino acid sequence having at least 98% homology with the amino acid sequence of SEQ ID NO:4.

23. A method for the production of a fungal xyloglucan endotransglycosylase enzyme (XET), comprising:
(a) culturing in a suitable nutrient medium a fungus expressing a fungal XET under conditions conducive to the production of the XET, wherein the XET comprises an amino acid sequence selected from the group consisting of:
the amino acid sequence of SEQ ID NO:1;
the amino aid sequence of SEQ ID NO:2;
the amino acid sequence of SEQ ID NO:4; and
an amino acid sequence having at least 95% homology with the amino acid sequence of SEQ ID NO:1, SEQ ID NO:2 or SEQ ID NO:4, and exhibiting XET enzyme activity; and
(b) recovering the XET from the nutrient medium.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 27 amino acids
      (B) TYPE: amino acid
      (C) STRANDEDNESS: single
      (D) TOPOLOGY: linear    (ii) MOLECULE TYPE: peptide    (xi) SEQUENCE DESCRIPTION: SEQ ID NO: 1:

Ala Glu Phe Cys Gly Gln Trp Asp Thr Gln Thr Val Gly Asn Tyr Ile
1               5                   10                  15

Val Tyr Asn Asn Leu Leu Gly Ala Gly Ser Ala
            20                  25

(2) INFORMATION FOR SEQ ID NO: 2:

(i) SEQUENCE CHARACTERISTICS:
      (A) LENGTH: 24 amino acids
      (B) TYPE: amino acid
      (C) STRANDEDNESS: single
      (D) TOPOLOGY: linear    (ii) MOLECULE TYPE: peptide    (xi) SEQUENCE DESCRIPTION: SEQ ID NO: 2:

Xaa Asp Phe Cys Gly Gln Trp Asp Asn Val Lys Asn Gly Pro Tyr Thr
1               5                   10                  15

Leu Tyr Asn Asn Leu Gly Gly Lys
            20

(2) INFORMATION FOR SEQ ID NO: 3:

(i) SEQUENCE CHARACTERISTICS:
      (A) LENGTH: 975 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO: 3:

GGATCCGAAT TCCAACTATC CTGCCCTCCT TTCAAGCGAA CACCATGAAG TTCTCCTCGG    60

CTCTGTTTCT GGCCGCTACG GCGGTCTTGG CTTCCGCCGC GCCGCTTGAG CGCCGCGCCG    120

-continued

```
ACTTTTGTGG TCAATGGGAC AACGTGAAGA ACGGACCTTA CACTCTTTAC AACAACCTGT      180

GGGGAAAAGA TGCTTCCGGA GCCTCCGGAT CGCAATGCAC CGGCGTCGAT AGCTTCAGCA      240

GCAACACCAT CGCTTGGCAC ACATCCTGGT CCTGGTCCGG TGCTCAGTAC AATGTCAAGT      300

CTTACGCAAA CGTGGTCGTC GACATCACCT CTAAGAAACT CAGCGCCATC AGCAGCATTA      360

ACAGCATCTG GCGCTGGGCT TACACGGGTA GCAACATTGT TGCCAATGTT GCCTACGATA      420

TCTTCACTTC ATCCACTGTC GGTGGTAGCG AGGAATATGA AATCATGATA TGGGTTGGTG      480

CTCTCGGTGG TGCTGGTCCG ATCTCATCTA CCGGCTCCCC TATTGCCACC GTTTCCCTTG      540

CAGGCTCCTC GTGGAAGCTC TACAAGGGC CCAACGGGCA GATGACCGTG TTCAGCTTCG      600

TCGCCGAGTC CAACGTGAAC AACTTCAGCG GTGACCTTAA CGCTTTCATC AAGTACCTCA      660

CCGGCAACCA GGGCCTTCCC GCCTCGCAAT ACATCAAGAG CATTGGCGCT GGCACTGAGC      720

CGTTCACGGG TTCCAACGCC AAGCTGACCA CTTCCTCCTA CACTGTCAGC TTCAGATAAC      780

TGTGAAGCTT TATGCTGCCC TTATGCATCA TCCTTGTACA TAGTTATCAC CAGGGGACTC      840

TTGTAAATAC GATTGCCTTA TTAACCGCCT GCATCTGCTT TCACACAATG GCATTTACCA      900

ATCAACAGTG CGCCTCGAAT CCGTAAAAGG TGGCTTAAAA AAAAAAAAAA AAAAAAAAA      960

AATTCCTGCG GCCGC                                                      975
```

(2) INFORMATION FOR SEQ ID NO: 4:

(i) SEQUENCE CHARACTERISTICS:
        (A) LENGTH: 244 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 4:

```
Met Lys Phe Ser Ser Ala Leu Phe Leu Ala Ala Thr Ala Val Leu Ala
 1               5                  10                  15

Ser Ala Ala Pro Leu Glu Arg Arg Ala Asp Phe Cys Gly Gln Trp Asp
            20                  25                  30

Asn Val Lys Asn Gly Pro Tyr Thr Leu Tyr Asn Asn Leu Trp Gly Lys
        35                  40                  45

Asp Ala Ser Gly Ala Ser Gly Ser Gln Cys Thr Gly Val Asp Ser Phe
    50                  55                  60

Ser Ser Asn Thr Ile Ala Trp His Thr Ser Trp Ser Trp Ser Gly Ala
65                  70                  75                  80

Gln Tyr Asn Val Lys Ser Tyr Ala Asn Val Val Asp Ile Thr Ser
            85                  90                  95

Lys Lys Leu Ser Ala Ile Ser Ser Ile Asn Ser Ile Trp Arg Trp Ala
           100                 105                 110

Tyr Thr Gly Ser Asn Ile Val Ala Asn Val Ala Tyr Asp Ile Phe Thr
       115                 120                 125

Ser Ser Thr Val Gly Gly Ser Glu Glu Tyr Glu Ile Met Ile Trp Val
   130                 135                 140

Gly Ala Leu Gly Gly Ala Gly Pro Ile Ser Ser Thr Gly Ser Pro Ile
145                 150                 155                 160

Ala Thr Val Ser Leu Ala Gly Ser Ser Trp Lys Leu Tyr Lys Gly Pro
               165                 170                 175

Asn Gly Gln Met Thr Val Phe Ser Phe Val Ala Glu Ser Asn Val Asn
           180                 185                 190
```

```
-continued

Asn Phe Ser Gly Asp Leu Asn Ala Phe Ile Lys Tyr Leu Thr Gly Asn
        195                 200                 205

Gln Gly Leu Pro Ala Ser Gln Tyr Ile Lys Ser Ile Gly Ala Gly Thr
        210                 215                 220

Glu Pro Phe Thr Gly Ser Asn Ala Lys Leu Thr Thr Ser Ser Tyr Thr
225                 230                 235                 240

Val Ser Phe Arg
```